US00PP30415P2

(12) United States Plant Patent
Li

(10) Patent No.: US PP30,415 P2
(45) Date of Patent: Apr. 16, 2019

(54) ***PORTULACA* PLANT NAMED 'KLEPO17022'**

(50) Latin Name: *Portulaca oleracea*
Varietal Denomination: KLEPO17022

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,606

(22) Filed: Mar. 22, 2018

(51) Int. Cl.
*A01H 5/02* (2018.01)

(52) U.S. Cl.
USPC ..... Plt./471

(58) Field of Classification Search
USPC ..... Plt./471
See application file for complete search history.

*Primary Examiner* — Annette H Para
(74) *Attorney, Agent, or Firm* — Bethany R. Roahrig; Cochran Freund & Young LLC

(57) ABSTRACT

A *portulaca* plant particularly distinguished by having large, bicolored magenta star patterned flowers, is disclosed.

1 Drawing Sheet

Genus and species: *Portulaca oleracea.*
Variety denomination: 'KLEPO17022'.

BACKGROUND OF THE NEW PLANT

The present invention comprises a new and distinct variety of *portulaca* plant, botanically known as *Portulaca oleracea*, and referred to by the variety name 'KLEPO17022'.

'KLEPO17022' originated from a cross-pollination made in December 2013 in Cobbitty, New South Wales, Australia. The female parent was an unpatented proprietary *portulaca* breeding line named 'PO01.00.12' and the male parent was an unpatented proprietary *portulaca* breeding line named 'PO02.00.12'.

Seeds from the cross-pollination were obtained and sown and plants were grown for evaluation. A single plant was selected in November 2014 and designated 'KLEPO17022'. In November 2014, 'KLEPO17022' was first vegetatively propagated by stem cuttings in Cobbitty, New South Wales, Australia. 'KLEPO17022' was found to reproduce true to type in successive generations of asexual propagation via stem cuttings.

SUMMARY

The following are the most outstanding and distinguishing characteristics of this new variety when grown under normal horticultural practices in Cobbitty, New South Wales, Australia.

1. Large flowers; and
2. Bicolored flowers having a magenta star with yellow edge.

DESCRIPTION OF THE PHOTOGRAPH

This *portulaca* plant is illustrated by the accompanying photograph which shows the plant's overall plant habit including form, foliage, and flowers. The photograph is of a 15-month old plant grown in Stuttgart, Germany. The plant was grown for four weeks in a glasshouse and afterwards outdoors in July 2016. The colors shown are as true as can be reasonably obtained by conventional photographic procedures.

DESCRIPTION OF THE NEW VARIETY

The following detailed descriptions set forth the distinctive characteristics of 'KLEPO17022'. The data which define these characteristics were collected from 5 month old plants in March 2018 in Cobbitty, New South Wales, Australia. Color references are to The R.H.S. Colour Chart of The Royal Horticultural Society of London (R.H.S.), 5$^{th}$ edition (2007).

Classification:
- *Family.*—Portulacaceae.
- *Botanical.*—*Portulaca oleracea.*
- *Common.*—Purslane.
- *Designation.*—'KLEPO17022'.

Parentage:
- *Female parent.*—'PO01.00.12' (unpatented).
- *Male parent.*—'PO02.00.12' (unpatented).

Plant description:
- *Habit and form.*—Compact and semi-trailing.
- *Height.*—3.5 cm.
- *Spread.*—28.0 cm.
- *Time and conditions to produce a rooted cutting.*—8 to 12 days.
- *Life cycle.*—Annual.
- *Flowering requirements.*—Spring to autumn.

Stems:
- *General description.*—Round with slight ridges.
- *Stem color.*—RHS 144A.
- *Anthocyanin color.*—RHS 176B.
- *Pubescence.*—Absent.
- *Stem diameter.*—2.5 mm to 3.5 mm.
- *Stem length.*—14.0 cm to 16.0 cm.
- *Internode length.*—1.5 cm to 2.2 cm.
- *Branching.*—Abundant.

Leaves:
- *Arrangement.*—Alternate.

*Shape*.—Oblanceolate.
*Apex*.—Acute in younger leaves but more rounded in mature leaves.
*Base*.—Obtuse.
*Margin*.—Entire.
*Leaf attachment*.—Petiolate.
*Leaf length*.—2.1 cm.
*Leaf width*.—1.0 cm.
*Leaf thickness*.—1.3 mm.
*Surface texture* (*both surfaces*).—Succulent, smooth.
*Leaf color*.—Upper surface: RHS 146A with RHS 61B at edge. Lower surface: RHS 146B with RHS 61C at edge.
*Leaf surface pubescence*.—Absent.
*Venation*.—Indistinguishable from leaf blade.
*Petiole length*.—1.2 mm.
*Fragrance*.—Absent.

Inflorescence:
*Inflorescence type*.—Terminal inflorescence, single flower.
*Flowering habit*.—Indeterminate.
*Time to bloom from propagation*.—6 to 8 weeks.
*Lastingness of individual blooms on the plant*.—1 to 3 days.
*Flower diameter*.—3.65 cm.
*Flower depth*.—1.7 cm.
*Fragrance*.—Absent.

Flower bud:
*Surface appearance and texture*.—Shiny, pubescent.
*Shape*.—Ovate.
*Bud length*.—1.3 cm.
*Bud diameter*.—0.65 cm.
*Bud color*.—RHS N144A with RHS 61B at edge.

Corolla:
*Arrangement*.—Single flower with five distinct petals, free.
*Petal shape*.—Ovate.
*Petal pubescence*.—Absent.
*Petal size*.—Length: 2.1 cm. Width: 1.8 cm.
*Petal apex*.—Rounded.
*Petal margin*.—Entire.
*Petal color* (*both surfaces*).—RHS N74B magenta stars with RHS 14B yellow edge and RHS155D white background.

Calyx:
*Arrangement*.—Composed of two sepals, free.
*Sepals*.—Shape: Deltoid. Apex: Acute. Margin: Entire. Sepal length: 1.1 cm. Sepal diameter: 0.8 cm. Sepal color: RHS 144B. Texture (both surfaces): Smooth. Appearance: Double lobed.

Reproductive organs: Androecium.
*Stamen number*.—Many.
*Stamen form*.—Free.
*Stamens color*.—Anther: RHS 17A. Filament color: RHS 42A.
*Stamen length*.—3.0 cm to 6.0 mm.
*Pollen amount*.—Medium.
*Pollen color*.—RHS 17A.
*Fragrance*.—Absent.
*Placental arrangement*.—Central.
*Pistil number*.—1 (per inflorescence).
*Pistil length*.—1.5 cm.
*Stigma color*.—RHS 61B.
*Stigma length*.—0.4 cm.
*Style length*.—1.1 cm.
*Style color*.—RHS 61B.
*Seed production*.—None observed to date.

Disease and insect resistance: None observed.

Environmental conditions, disease and insect resistance: None observed.

COMPARISON WITH PARENTAL LINES AND KNOWN VARIETY

'KLEPO17022' is a distinct variety of *portulaca* owing to its magenta star patterned flower color. 'KLEPO17022' is distinguished from its parents as shown below in Table 1.

TABLE 1

Comparison with Parental Lines

| Characteristic | 'KLEPO17022' | Female parent: 'PO01.00.12' | Male parent: 'PO02.00.12' |
|---|---|---|---|
| Bicolor flower pattern | Stable | Unstable | Unstable |
| Flower size | Large | Medium | Medium |

'KLEPO17022' is most similar to the variety DUNA 'Pink Star' (unpatented) however, there are differences as described in the table below.

TABLE 2

Comparison with Similar Variety

| Characteristic | 'KLEPO17022' | DUNA 'Pink Star' |
|---|---|---|
| Bicolor flower pattern | Magenta star with yellow edge | Pink star with white edge |
| Braching | More secondary branches than DUNA 'Pink Star' | Less secondary branches than 'KLEPO17022' |

I claim:

1. A new and distinct variety of *portulaca* plant named 'KLEPO17022' as illustrated and described herein.

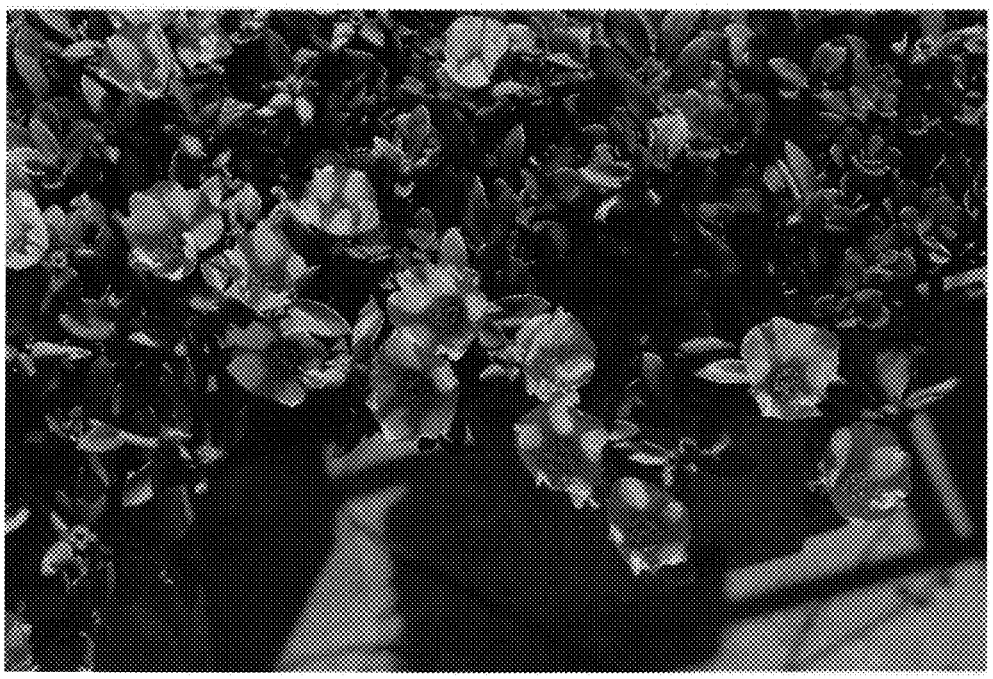

* * * * *